United States Patent
Fava et al.

(10) Patent No.: US 11,094,321 B2
(45) Date of Patent: Aug. 17, 2021

(54) VOICE CONTROL SYSTEM FOR OPHTHALMIC LASER SYSTEMS

(71) Applicant: NORLASE ApS, Ballerup (DK)

(72) Inventors: Greg Fava, Redwood City, CA (US); Peter Skovgaard, Birkerod (DK)

(73) Assignee: Norlase APS, Ballerup (DK)

( * ) Notice: Subject to any disclaimer, the term of this patent is extended or adjusted under 35 U.S.C. 154(b) by 91 days.

(21) Appl. No.: 16/133,253

(22) Filed: Sep. 17, 2018

(65) Prior Publication Data
US 2019/0019514 A1 Jan. 17, 2019

Related U.S. Application Data

(63) Continuation-in-part of application No. PCT/EP2018/052896, filed on Feb. 6, 2018.
(Continued)

(30) Foreign Application Priority Data

Sep. 11, 2017 (DK) .............................. PA201770679

(51) Int. Cl.
*G10L 15/00* (2013.01)
*G10L 15/22* (2006.01)
(Continued)

(52) U.S. Cl.
CPC .............. *G10L 15/22* (2013.01); *A61B 17/00* (2013.01); *A61F 9/008* (2013.01);
(Continued)

(58) Field of Classification Search
CPC combination set(s) only.
See application file for complete search history.

(56) References Cited

U.S. PATENT DOCUMENTS

| 4,917,486 A | 4/1990 | Raven et al. |
| 5,147,349 A | 9/1992 | Johnson et al. |

(Continued)

FOREIGN PATENT DOCUMENTS

| WO | WO 02/083041 | 10/2002 |
| WO | WO 2008/106590 | 9/2008 |

(Continued)

OTHER PUBLICATIONS

Extended European Search Report, dated Jan. 22, 2020, from European Application No. 19196932.8, filed on Sep. 12, 2019. 7 pages.
(Continued)

*Primary Examiner* — Vu B Hang
(74) *Attorney, Agent, or Firm* — HoustonHogle LLP

(57) ABSTRACT

A voice control system for ophthalmologic laser treatment systems sets parameters for delivering laser energy based on voice commands and prevents potentially harmful parameters due to operator mistakes and misunderstood voice commands by providing incremental parameter adjustment and restricting the amount by which the parameters can be adjusted for each executed voice command. Valid voice commands include indications of which parameter to set, a value for the parameter, and whether to increase or decrease the value of the parameter. In one example, parameter values can only be increased or decreased by a certain percentage with respect to the current value. In another example, the parameters are adjusted by selecting the next highest or lowest value with respect to the current parameter value from a predetermined sequence of possible values for particular parameters. Voice control functionality can also be deactivated under certain conditions such as when it is determined that a parameter was not set.

34 Claims, 8 Drawing Sheets

Related U.S. Application Data

(60) Provisional application No. 62/456,829, filed on Feb. 9, 2017.

(51) Int. Cl.
*A61F 9/008* (2006.01)
*A61B 17/00* (2006.01)
*G10L 15/07* (2013.01)
*G10L 15/08* (2006.01)

(52) U.S. Cl.
CPC ..... *A61F 9/00821* (2013.01); *A61B 2017/00203* (2013.01); *A61F 2009/00863* (2013.01); *A61F 2009/00868* (2013.01); *A61F 2009/00891* (2013.01); *G10L 15/07* (2013.01); *G10L 15/08* (2013.01); *G10L 2015/223* (2013.01); *G10L 2015/225* (2013.01)

(56) References Cited

U.S. PATENT DOCUMENTS

| | | | |
|---|---|---|---|
| 5,954,711 | A | 9/1999 | Ozaki et al. |
| 6,370,168 | B1 | 4/2002 | Spinelli |
| 7,921,017 | B2 | 4/2011 | Claus et al. |
| 2004/0057119 | A1 | 3/2004 | Sagehashi et al. |
| 2004/0078029 | A1 | 4/2004 | Momiuchi et al. |
| 2005/0026745 | A1 | 2/2005 | Mitrovic |
| 2008/0021711 | A1* | 1/2008 | Claus .............. A61B 17/00 704/275 |
| 2011/0098692 | A1 | 4/2011 | Shazly et al. |
| 2013/0253411 | A1 | 9/2013 | Rubinchik et al. |
| 2015/0290031 | A1* | 10/2015 | Wellhoefer .......... A61F 9/008 345/156 |
| 2015/0366713 | A1 | 12/2015 | Shazly et al. |
| 2016/0270656 | A1* | 9/2016 | Samec ................ A61B 3/1216 |
| 2016/0346126 | A1 | 12/2016 | Luttrull et al. |

FOREIGN PATENT DOCUMENTS

| | | |
|---|---|---|
| WO | WO 2013/059564 | 4/2013 |
| WO | WO 2015/170947 | 11/2015 |
| WO | WO 2017/122061 | 7/2017 |
| WO | WO 2018/146070 | 8/2018 |

OTHER PUBLICATIONS

Masui, S., et al. "Recent Improvement in Nitride Lasers," Gallium Nitride Materials and Devices XII, edited by Jen-lnn Chyi et al., Proc. of SPIE vol. 10104: 101041H-1-101041H-8 (2017).

Masui, S., et al., "1 W AlInGaN Based Green Laser Diodes," 2013 Conference on Lasers and Electro-Optics Pacific Rim, Optical Society of America, paper WH3_1 (2013).

Willstrand, O. "Intensity distribution conversion from Gaussian to Top-Hat in a single-mode fiber connector", Master's Thesis, Lund University, Sweden, Jan. 25, 2013.

Becker, B. C., et al., "Semiautomated intraocular laser surgery using handheld instruments," Lasers Surg. Med., 42(3): 264-273 (2010).

Yang, S., et al., "Handheld-automated microsurgical instrumentation for intraocular laser surgery," Lasers Surg. Med., 47 (8): 658-668 (2015).

* cited by examiner

VOICE CONTROL SYSTEM FOR OPHTHALMIC LASER SYSTEMS

RELATED APPLICATIONS

This application is a Continuation-in-Part of International Patent Application No. PCT/EP2018/052896, filed on Feb. 6, 2018, which designates the United States. International Application No. PCT/EP2018/052896, in turn, claims the benefit under 35 U.S.C. § 119(e) of U.S. Provisional Application No. 62/456,829, filed on Feb. 9, 2017, and further claims priority to Danish Patent Application No. PA201770679, filed on Sep. 11, 2017, all of which are incorporated herein by reference in their entirety.

BACKGROUND OF THE INVENTION

There are a number of treatment regimes that involve delivering laser energy to a patient's eye. In these treatments, doctors regularly set and update parameters dictating the laser energy to be delivered. These parameters can include peak power, pulse duration, and repeat interval, among other examples.

Commonly, slit lamps are used for delivering the laser energy to the patient's eye. In these systems, the patients sit up in an examination chair, rest their chin on a chin rest, and place their forehead against a forehead band, both of which keep the patient's head in place during the procedure.

Another common device is a Laser Indirect Ophthalmoscope (LIO), which is a head mounted device, worn by the doctor to deliver laser energy into a patient's eye. Current systems use a laser console for generating the laser light and a long fiber optic umbilical coupled to the LIO. The laser console includes a laser source, a power source (for example, providing AC/DC conversion), laser drive and parameter control systems, and a user interface. The user interface comprises physical knobs and switches or a touchscreen and can be part of the laser console itself or a remote control device that communicates with the laser console. Activation devices (e.g. footswitches) connect to the laser consoles and activate the laser emission, for example, by sending an activation signal to the laser console in response to engagement of an activation mechanism (e.g. compression of the footswitch).

During procedures using the LIO, the doctor moves the laser console, which is positioned on a cart or table, to be in the proximity of the patient who is usually in a supine position. The doctor then walks around the patient to deliver the laser energy to the desired portions of the retina. If a parameter change is needed, the doctor physically returns to the laser console to make the change or has an assistant, for example, standing next to the laser console, make the change.

SUMMARY OF THE INVENTION

The present invention includes a voice control system for ophthalmologic laser treatment systems that is robust against operator mistakes and misunderstood commands, for example, by replaying and confirming voice commands, evaluating desired parameters against a predetermined safety policy, and providing incremental parameter adjustment and restricting the amount by which the parameters can be increased and/or decreased for each executed voice command. The voice control system includes a voice control module for recognizing spoken commands and a parameter regulation module for generating parameter information based on the spoken commands and a predetermined safety policy. Audible feedback of current and updated parameters is also provided.

In one example, a microphone first detects a wake word (which is a special phrase to indicate that verbal commands follow). The wake word provides a two-step recognition requirement for voice commands in order to make a parameter change, decreasing the likelihood of an erroneous parameter change. In one embodiment, a tone is played after the wake word is detected to prompt the user to provide the voice command.

In response to detecting the wake word, and after the tone is played, the microphone captures audio data, and the voice control module recognizes in the audio data a spoken command (in any multitude of languages) from a predetermined set of commands. The parameter regulation module then generates the parameter information based on which commands and other spoken information were recognized by the voice control module.

In one example, the parameter regulation module only increases the power and duration set points by 20% or less of the current set points, and the valid voice commands are limited to indicating which parameter to adjust and whether to adjust the parameter up or down. These voice commands can include "Power up," "Power down," "Duration up," "Duration down," "Interval up," "Interval down," "Aiming beam up," and "Aiming beam down," to list a few examples. The amount by which the parameters can be increased or decreased can be restricted based on multiple considerations, including, for example, a prescribed tolerance band for set parameters according to industry regulations.

Additionally, the voice control functionality can be selectively executed under certain conditions to further enhance the safety of the laser treatment system. In one example, voice commands to change the interval parameter are not executed when it is determined that the user had not previously specified a repeat interval for the current laser treatment session.

In general, according to one aspect, the invention features a system for delivering laser energy to an eye of a patient comprising a microphone, a voice control module, an parameter regulation module, and a control module. The microphone captures audio data. The voice control module receives the captured audio data and generates voice command information based on the captured audio data. The parameter regulation module generates parameter information based on the voice command information. The control module receives the parameter information and sets the parameters for the delivered laser energy based on the parameter information.

In embodiments, the voice control module generates the voice command information by recognizing spoken language in the captured audio data, which can indicate the parameters to be adjusted, values for the parameters and/or whether values for the parameters should be increased or decreased. The microphone captures the audio data in response to detecting a predetermined wake word, and audible feedback confirming the parameter information and/ or the voice command information is provided via speakers. Both the voice control module and the parameter regulation module can execute on a mobile computing device of a body-mounted laser-indirect ophthalmoscope system, a laser console of a laser-indirect ophthalmoscope system, and/or a user terminal of an ophthalmic laser treatment system. The parameter regulation module generates the parameter information based on current values for the parameters to be set and/or a predetermined safety policy, which can indicate maximum values and/or percentages by which the parameters can be increased and/or decreased, predetermined sequences of possible values for the parameters, whether setting of parameters in response to voice commands is selectively executed based on the current parameters, and/or other criteria indicating that the parameters are potentially unsafe.

In general, according to another aspect, the invention features a method for delivering laser energy to an eye of a patient using an ophthalmic laser treatment system. Audio data is captured, and voice command information based on the captured audio data is generated. Parameter information is then generated based on the voice command information. The parameters for the delivered laser energy are set based on the parameter information.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

The present invention concerns a voice control system for different ophthalmic laser treatment devices. In general, FIGS. 1-6 concern exemplary ophthalmic laser treatment systems that have been augmented according to the present invention.

Figure 1:
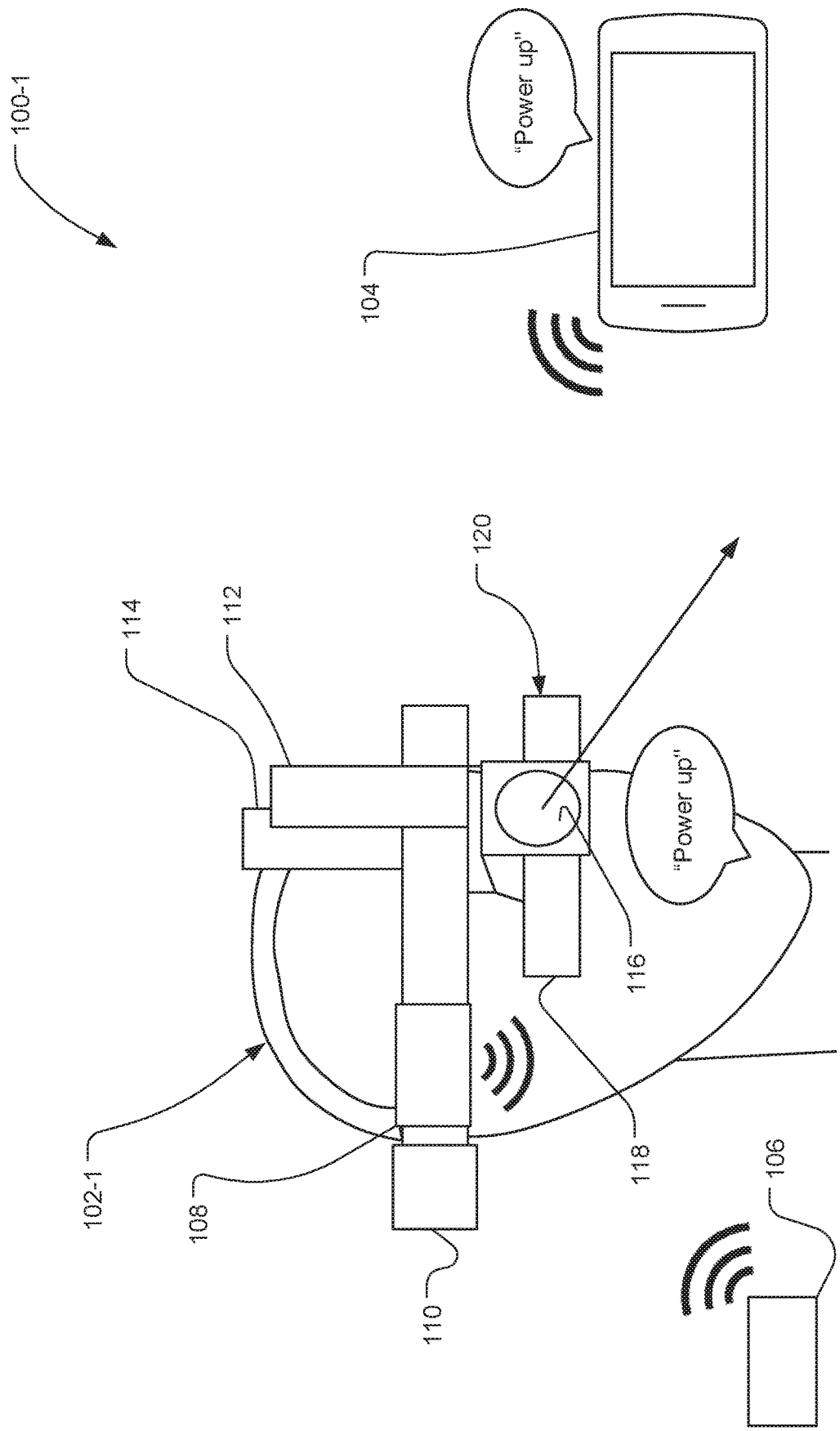
FIG. 1 is a schematic illustration of an exemplary body-mounted laser-indirect ophthalmoscope (LIO) system to which the present invention is applicable.

FIG. 1 is an illustration of a body-mounted LIO system 100-1. In general, the body-mounted LIO system 100 delivers laser energy to an eye of a patient. A user of the LIO system 100-1 is typically a doctor such as an ophthalmologist.

The body-mounted LIO system 100-1 includes a binocular indirect ophthalmoscope 120, a control module 108, a power module 110, a laser module 112 and a mobile computing device 104.

The binocular indirect ophthalmoscope 120 is an optical device for examining the inside of the eye of the patient. The binocular indirect ophthalmoscope 120 includes an illumination unit 114 for providing white light and an optical system including a viewing aperture 118 and an exit aperture 116 from which the laser energy is emitted (which is also an entrance aperture for image information e.g. for viewing the patient's eye).

In general, the power module 110 provides power to the control module 108 and the laser module 112. In one embodiment, the power module 110 also provides power to the illumination unit 114 of the binocular indirect ophthalmoscope 120.

The laser module 112 produces and emits the pulsed laser energy according to certain user-provided parameters such as pulse envelope duration, peak power, and micropulse duration and interval, among other examples.

The activation device 106, which is part of the user interface of the body-mounted LIO system 100-1, is a device that receives user input via an activation mechanism (e.g. a switch or button) and in response sends activation signals to the control module 108 indicating that the laser energy should be emitted. The activation device 106 is typically a footswitch, and engagement with the activation mechanism includes compression of the footswitch by the user's foot, for example.

Preferably, the mobile computing device 120 is a tablet computer. Alternatively, the mobile computing device 120 could be a smartphone device, laptop computer, or phablet computer (i.e., a mobile device that is typically larger than a smart phone, but smaller than a tablet), to list a few examples. In general, the mobile computing device 104 provides additional components of the user interface and generates parameter information indicating the user-provided parameters based on input received via the user interface and sends the parameter information to the control module 108.

In the illustrated example, the user interface further includes a voice control interface that allows the user to indicate parameter information using verbal commands. In one example, the user provides a verbal command (e.g. "Power 200", "Power up"), and the mobile computing device provides audible feedback confirming the command, for example, by calling out the parameter being adjusted. In one example, if the "power" is currently set at 200, and a voice command of "Power up" is given, the audible feedback calls out the name of the parameter and the next highest increment from the starting point (e.g. "Power at 225").

The control module 108 controls the laser energy delivered by the laser module 112 based on parameter information received from the mobile computing device 104 and activation signals received from the activation device 106. In the illustrated example, the control module 108 communicates with the activation device 106 and the mobile computing device 104 wirelessly. In response to receiving the parameter information from the mobile computing device 104, the control module 108 sets the parameters for the laser energy. In response to receiving activation signals from the activation device 106, the control module 108 sends control signals reflecting the user-provided parameters to the laser module 112 activating the laser module and causing it to produce and/or emit the laser energy.

The body-mounted LIO system 100-1 includes a wearable assembly 102, which secures the body-mounted LIO system 100-1 to the user's body via one or more wearable objects such as a headset, a utility belt, or a backpack, among other examples. In the illustrated example, the wearable assembly 102 comprises only a headset 102-1, which is worn on the user's head.

Figure 2:
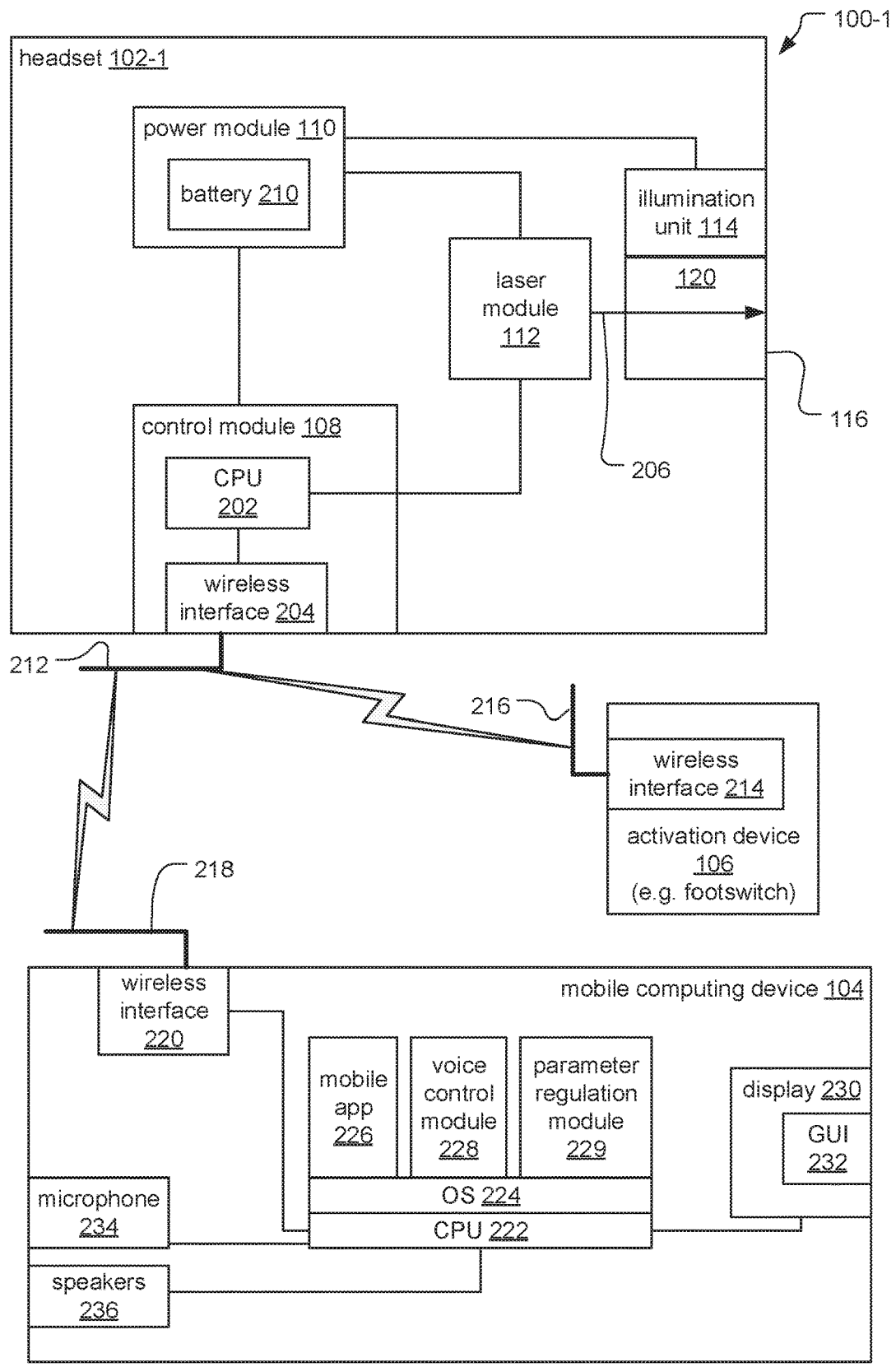
FIG. 2 is a block diagram of the body-mounted LIO system according to the present invention.

FIG. 2 is a block diagram of the body-mounted LIO system 100-1 according to the preferred embodiment showing the components of the system in more detail. Specifically, internal components of the headset 102-1, the activation device 106, and the mobile computing device 104 are shown.

The mobile computing device 104 includes a central processing unit (CPU) 222, a touchscreen display 230, a wireless interface 222 and antenna 218, a microphone 234 and speakers 236.

The CPU 222 executes firmware/operating system instructions and sends instructions and data to and receives data from the wireless interface 220, the microphone 234, the speakers 236, and the display 230. Executing on typically an operating system (OS) 224 of the CPU 222 are a mobile application 226, a voice control module 228, and an parameter regulation module 229. The mobile application 226 renders a graphical user interface (GUI) 232 on the touchscreen display 230. The GUI 232, which is part of the user interface of the body-mounted LIO system 100-1, displays and receives information such as parameter information, for example, by detecting contact between the user and the touchscreen display 230 in certain regions of the touchscreen display 230. The mobile application 226 also performs functions related to configuring the LIO system 100 such as pairing the mobile computing device 104 with the control module 108 and/or setting a wake word, which is a selected phrase for indicating that verbal commands follow.

The microphone 234 captures sound including the wake word and voice commands indicating parameter information provided by the user, which the mobile computing device 104 converts to audio data.

The speakers 236 produce sound based on instructions from the parameter regulation module 229, for example, in order to provide audible feedback confirming parameter information and/or voice commands.

The voice control module 228 generates voice command information based on the captured audio data. In one example, the voice control module 228 recognizes spoken language in the audio data and translates the spoken language to commands that can be interpreted by the parameter regulation module 229 and/or executed by the control module 108.

The parameter regulation module 229 generates parameter information based on the voice command information generated by the voice control module 228, current parameters for delivering the laser energy, and/or a predetermined safety policy. In generating the parameter information, the parameter regulation module 229 also controls and limits the ability of voice commands generated by the voice control module to enact changes to the parameters for the delivered laser energy.

The parameter regulation module 229 maintains a set of voice commands that are recognized and translated to parameter information. These valid voice commands might include indicating which parameter to set or adjust and what value to set for the parameter or whether to adjust the parameter up or down in order to provide incremental voice command functionality. These voice commands can include "Power 200," "Power up," "Power down," "Duration up," "Duration down," "Interval up," "Interval down," "Aiming beam up," "Aiming beam down," "Pulse duration up," "Pulse duration down," to list a few examples.

The parameter regulation module 229 further provides the audible feedback confirming the voice command information and/or parameter information by sending instructions to the speakers 236 to produce sound, for example, repeating back the voice commands interpreted by the parameter regulation module 229 and/or parameter information. Additionally, the parameter regulation module 229 evaluates the generated parameter information against a predetermined safety policy (for example, based on predetermined criteria in the safety policy for determining when parameters are potentially unsafe) and seeks extra confirmation of the voice command information and/or the parameter information if the parameter information is determined to be unsafe based on the safety policy.

In one example, the parameter regulation module 229 provides audible feedback repeating the voice command and then waits for input from the user interface (e.g. further voice command information generated by the voice control module 228 based on sound detected by the microphone 234) before proceeding to generate the parameter information.

In another example, the parameter regulation module 229 determines that the parameters indicated by the parameter information generated based on the voice command information are unsafe and alerts the user (e.g. via sound produced by the speakers 236) that the parameters are unsafe and/or requires extra confirmation from the user (e.g. via sound captured by the microphone 234) before proceeding to send the parameter information to the control module 108.

Additionally, in some embodiments, the parameter regulation module 229 generates the parameter information, for example, by increasing or decreasing current parameter values by predetermined values or percentages. In one example, the parameter regulation module 229 calculates an adjusted parameter value that is no more than a predetermined percentage of the current value. The predetermined percentage for setting the power parameter might be 20%, meaning that the power parameter can only be increased and/or decreased by 20% of the current value in response to voice commands. Similarly, the voice commands "aiming beam up" or "aiming beam down" results in no greater than a 10% change in intensity.

In some embodiments, the parameter regulation module 229 iterates through sequences of predetermined values for particular parameters, selecting from the predetermined sequence a value that is higher or lower than the current parameter value in response to the voice command information. For example, a finite set of all possible power settings indicated by the predetermined safety policy might include 50, 60, 70, 80, 90, 100, 110, 120, 130, 140, 150, 175, 200, 225, 250, 275, 300, 325, 350, 375, 400, 425, 450, 475, 500 milliwatts (mW), continuing in 50 mW increments to 1500 mW. If the current power setting is at 100 mW, the parameter regulation module 229 would generate parameter information indicating that the parameters should be set to 110 mW in response to the voice command "power up" and 90 mW in response to the voice command "power down." In this way, the parameter regulation module 229 prevents the parameters from being inadvertently adjusted from 100 mW to 1500 mW, for example, in response to a misspoken or misunderstood voice command. In a similar example, a finite set of all possible duration settings indicated by the predetermined adjustment criteria might include 10, 11, 12, 13, 14, 15, 17, 20, 22, 25, 30, 35, 40, 45, 50, 60, 70, 80, 90, 100, 112, 125, 150, 175, 200, 225, 250, 300, 350, 400, 450, 500, 600, 700, 800, 900, 1000 milliseconds (ms).

The parameter regulation module 229 also determines whether particular parameters can or can not be set in response to voice commands based on the current parameter information. For example, the parameter regulation module 229 might determine that the interval setting was set to "OFF", or that no interval parameter value was initially provided, and automatically ignore voice commands for the interval parameter in order to prevent the interval parameter from being accidentally set. In this way, the module 229 applies a safety policy that prevents the operator from changing the parameters in a way that could be detrimental to patient health.

In the illustrated example, the voice control module 228, microphone 234, speakers 236, GUI 232 rendered on the touchscreen display 230, and the activation device 106 provide a general user interface (UI) for the LIO system 100. However, in other embodiments (not illustrated) the UI for the LIO system 100 can also include other user interface elements 237 such as physical input mechanisms such as knobs or buttons, which can be part of the mobile computing device 104 itself or part of peripheral devices connected to the mobile computing device 104 via the wireless interface 220 and/or a physical interface (e.g. data port). In general, the parameter information can be generated by the mobile computing device 104 based on any user engagement with the mobile computing device 104 and/or peripheral devices.

The wireless network interface 220 facilitates sending the parameter information to the control module 108 via the antenna 218 through a wireless communication link with the control module 108 according to wireless personal area network (WPAN) or wireless local area network (WLAN) protocols such as Bluetooth Low Energy (BLE) or WiFi, among other examples.

The headset 102-1, as previously discussed, includes the control module 108, the power module 110, the laser module 112, the binocular indirect ophthalmoscope 120 and the illumination unit 114.

The power module 110 includes a battery 210, which supplies the power provided to the control module 108, laser module 112 and illumination unit 114. Among other functions, the power module 110 performs the functions of a battery management system (e.g. preventing the battery from operating outside its Safe Operating Area, monitoring its state, etc.).

The laser module 112 includes a fiber optic cable 206 for emitting the laser energy. The fiber optic cable 206 is routed through the binocular indirect ophthalmoscope 120 such that the laser energy is emitted from the exit aperture 116.

The control module 108 includes a CPU 202 and a wireless interface 204. The CPU 202 directs the functionality of the control module 108 such as receiving parameter information from the mobile computing device 104 and activation signals from the activation device 106 via the wireless interface 204 and an antenna 212, as well as sending control signals to the laser module 112.

Finally, the activation device 106 includes a wireless interface 214 and an antenna 216 through which activation signals are sent to the control module 108. In another embodiment of the body-mounted LIO system 100-1 (not illustrated), the activation device 106 is a wired foot switch with a wired interface through which activations are sent to the control module 108.

In some embodiments, the voice control module also performs the functions of user interface associated with the activation device. For example, in response to a voice command such as "execute", the device could activate the laser.

Figure 3:
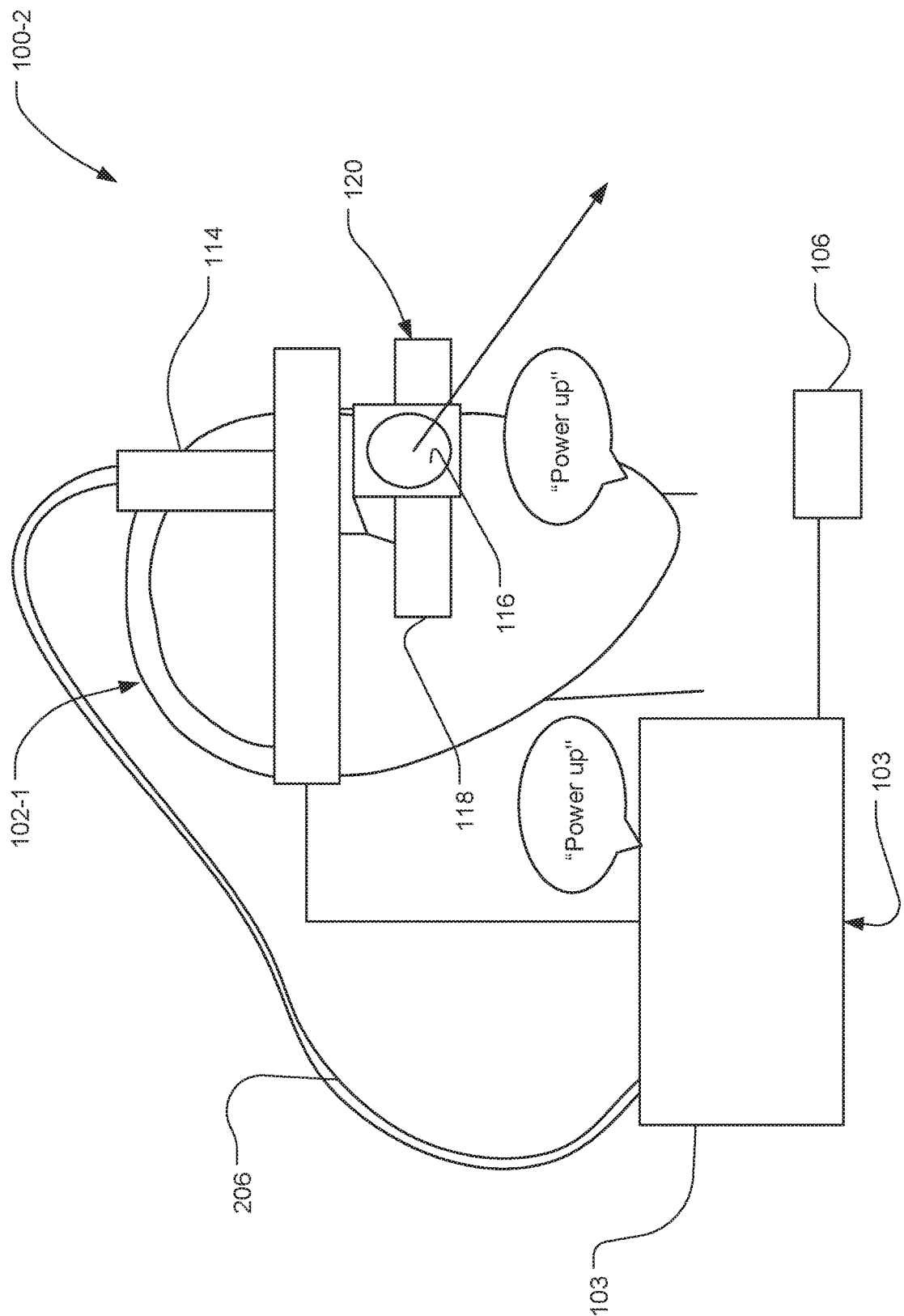
FIG. 3 is a schematic illustration of an exemplary table-top LIO system to which the present invention is also applicable.

FIG. 3 is an illustration of a table-top LIO system 100-2 to which the present invention is applicable.

The table-top LIO system 100-2 includes a laser console 103 and a headset 102-2. The headset 102-2 includes the binocular indirect ophthalmoscope 120 and the illumination unit 114 as before. Now, however, the laser console receives the user input via a user interface of the laser console 103, which can include a graphical user interface 232, or other input and display elements such as knobs, dials, keypads and/or buttons generates the parameter information, and drives the laser via a longer fiber optic cable 206 which is routed to the laser console 103. The laser console 103 receives input from the activation device 106 via a wired connection.

Figure 4:
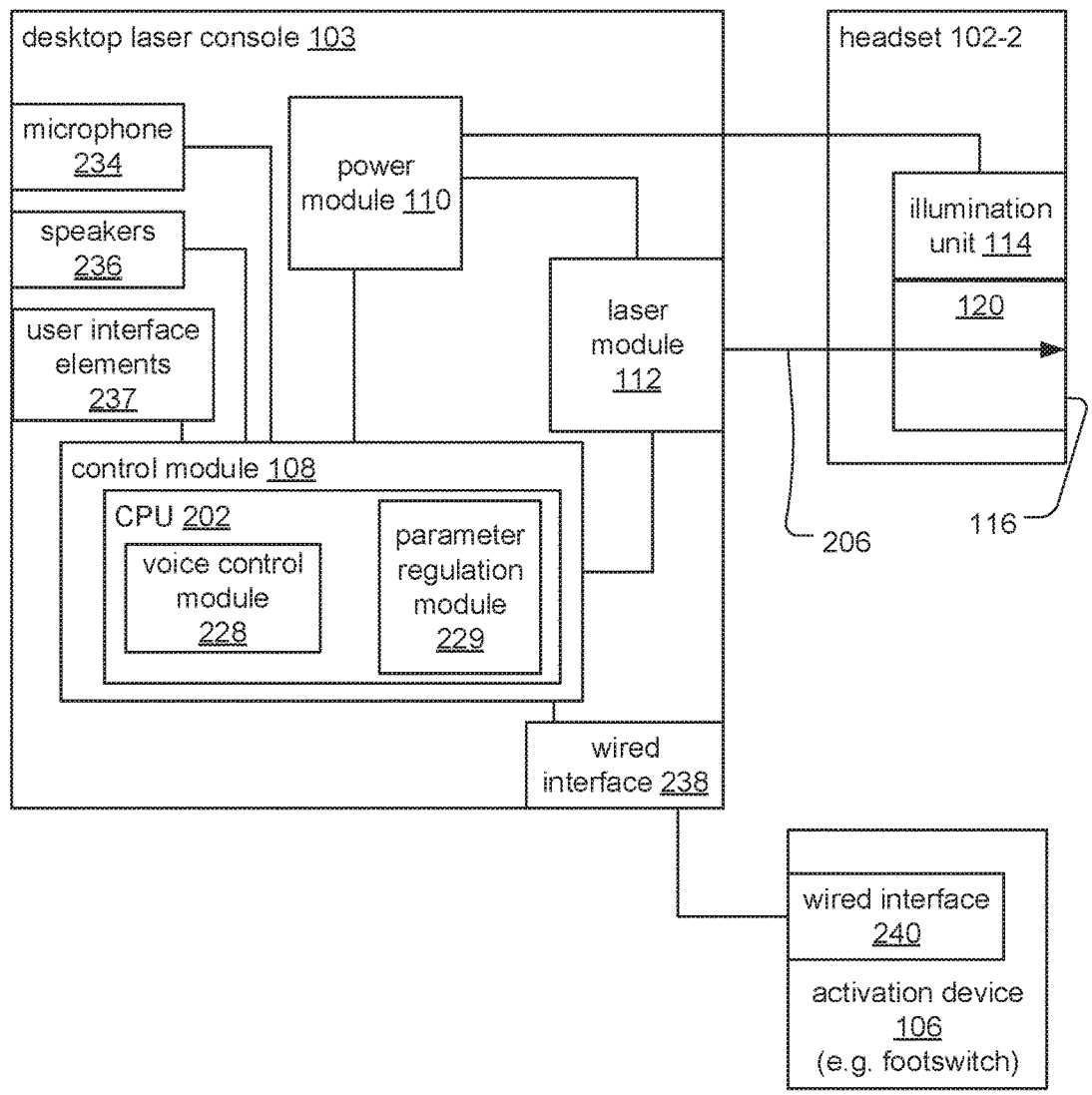
FIG. 4 is a block diagram of the table-top LIO system according to the present invention.

FIG. 4 is a schematic diagram of the table-top LIO system 100-2. Here, the laser console 103 includes the control module 108, the power module 110 and the laser module 112. Additionally, the activation device 106 includes a wired interface 240, and likewise the control module 108 includes a wired interface 238. Instead of sending the activation signals wirelessly to the control module 108, the activation device 106 sends the signals via a wired connection between the two devices.

Additionally, the laser console 103 now includes the microphone 234 and the speakers 236. The laser console 103 receives the user input via the graphical user interface 232 and/or an additional physical user interface 237, which can include input and display elements such as knobs, dials, keypads and/or buttons.

The control module 108, as before, sets the parameters for the delivered laser energy based on parameter information.

Now, additionally, the voice control module 228 and the parameter regulation module 229 execute on the CPU 202 of the control module 108.

Figure 5:
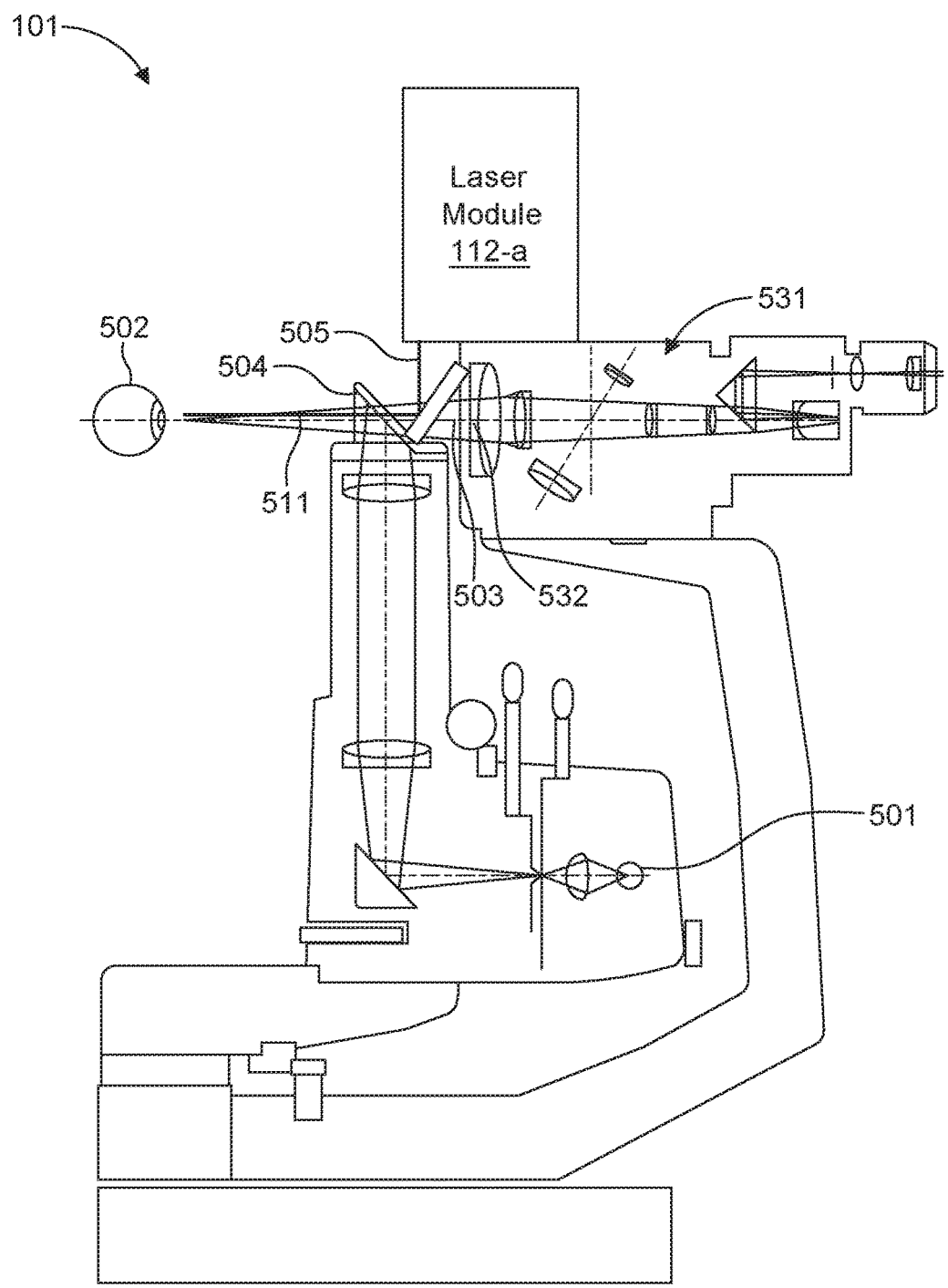
FIG. 5 is a schematic side cross-sectional view of an exemplary slit lamp system to which the present invention is also applicable.

FIG. 5 schematically shows a slit lamp device 101 to which the present invention is applicable. The figure schematically shows the previously described laser module 112-a that produces the pulsed laser energy and that is attached to the slit lamp 101 via a tonometer mount. The slit lamp includes a magnifying optical device 531, such as a microscope or zoom telescope, configured to receive light at a viewing input 532 along a viewing path 503 from a target area. The central part of the slit lamp 101 includes a white light source 501 that is used to illuminate a target area in the eye 502 of the patient. This white light is directed, by means of a mirror 504, onto an illumination output path 511 that coincides with the optical viewing path 503 of the operator at the designed focal point of the diagnostic instrument at the target area. In the same fashion, the light 505 from the laser is directed towards the target area along a treatment beam path such that it coincides with the viewing path, at least at the target area.

Figure 6:
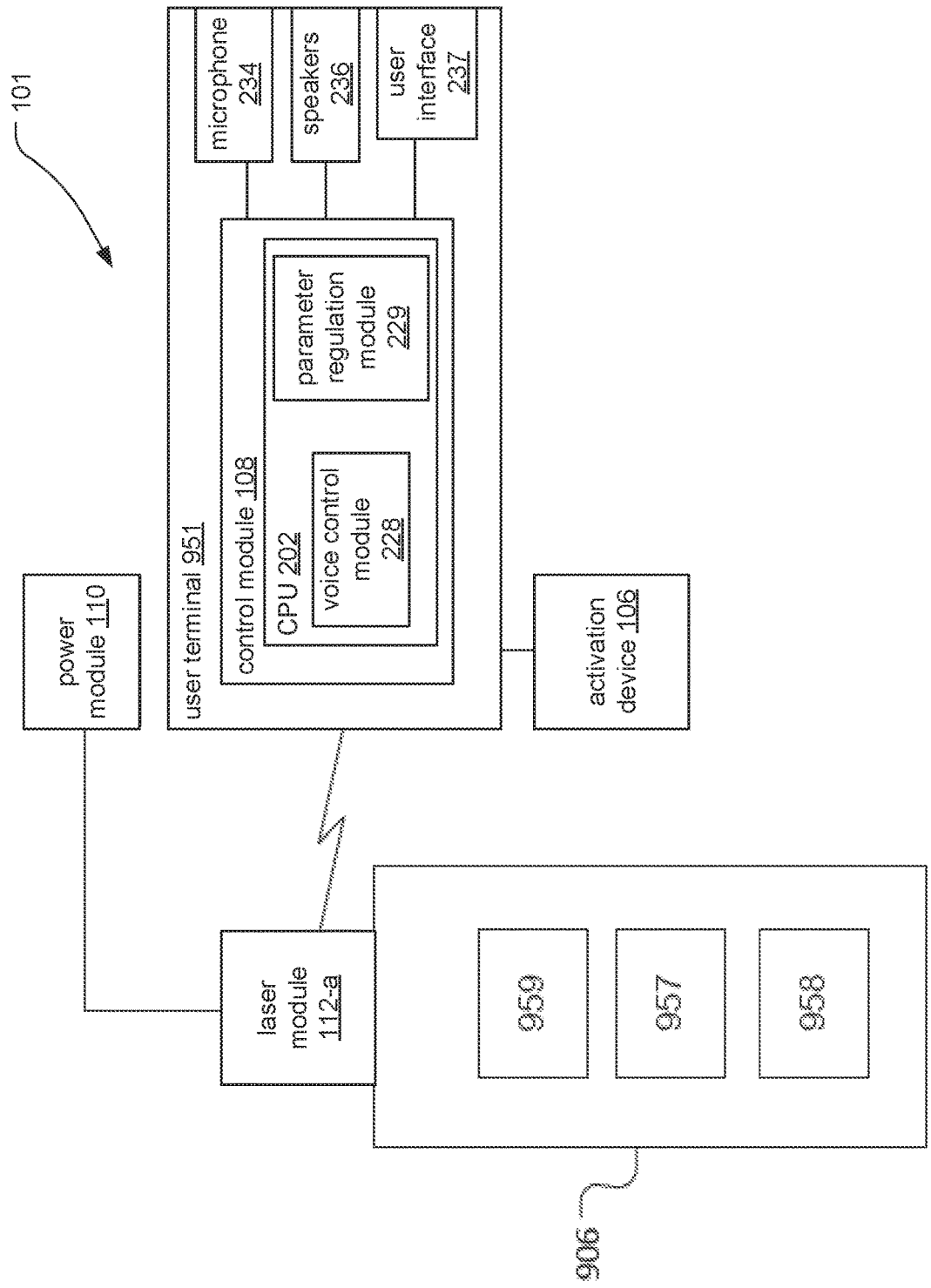
FIG. 6 is a block diagram of the slit lamp system according to the present invention.

FIG. 6 is a schematic diagram of the slit lamp device 101. The slit lamp device 101 comprises a diagnostic instrument 906 and an adapter unit 112-a mounted to the diagnostic instrument 906.

The system further comprises a user terminal 951 in wireless communication with the adapter unit 112-a, and the power module 110 electrically coupled to the adapter unit 112-a.

In the illustrated embodiment, the power module 110 provides DC operating power to the adapter unit 112-a and the user terminal 951 provides the user interface 237 to the operator and communicates control commands to the adapter unit 112-a. The power module 110 may be battery-powered or configured to receive external power, e.g. AC power. The power module 110 may also be integrated into or directly attached to the housing of the adapter unit 112-a; for example, the adapter unit 112-a may comprise a replaceable, e.g. rechargeable, battery. The user terminal 951 may further receive values of operational parameters such as performance parameters from the adapter unit. The power module 110 and the user terminal 951 may be embodied as separate units or as a single control unit. The user terminal 951 provides a voice interface allowing for a hands-free control of performance parameters of the adapter unit 112-a. To this end, the user terminal 951 includes the microphone 234, and speakers 236 and the voice control module 228 and parameter regulation module 229 execution on the CPU 202. Preferably, the voice recognition system is a self-contained system that operates without the need to communicate with a remote host. However, in alternative embodiments, the voice recognition system may be a distributed system where at least a part of the voice recognition process is performed by a remote host system. Alternatively or additionally, the user terminal may comprise one or more other user interface devices 237, such as knobs, switches, a display, a touch screen and/or the like. The user terminal may further comprise, or be coupled to, the activation device 106.

The diagnostic instrument comprises a power supply 959, a control unit 957 and an operating console 958, e.g. embodied as separate units or as a single, integrated unit. The user terminal 951 for controlling the adapter unit 112-a may be integrated into or separate from the operating console of the diagnostic instrument. Similarly, the power supply unit 952 and the power supply unit 959 may be embodied as separate units or as a single, integrated power supply.

Figure 7:
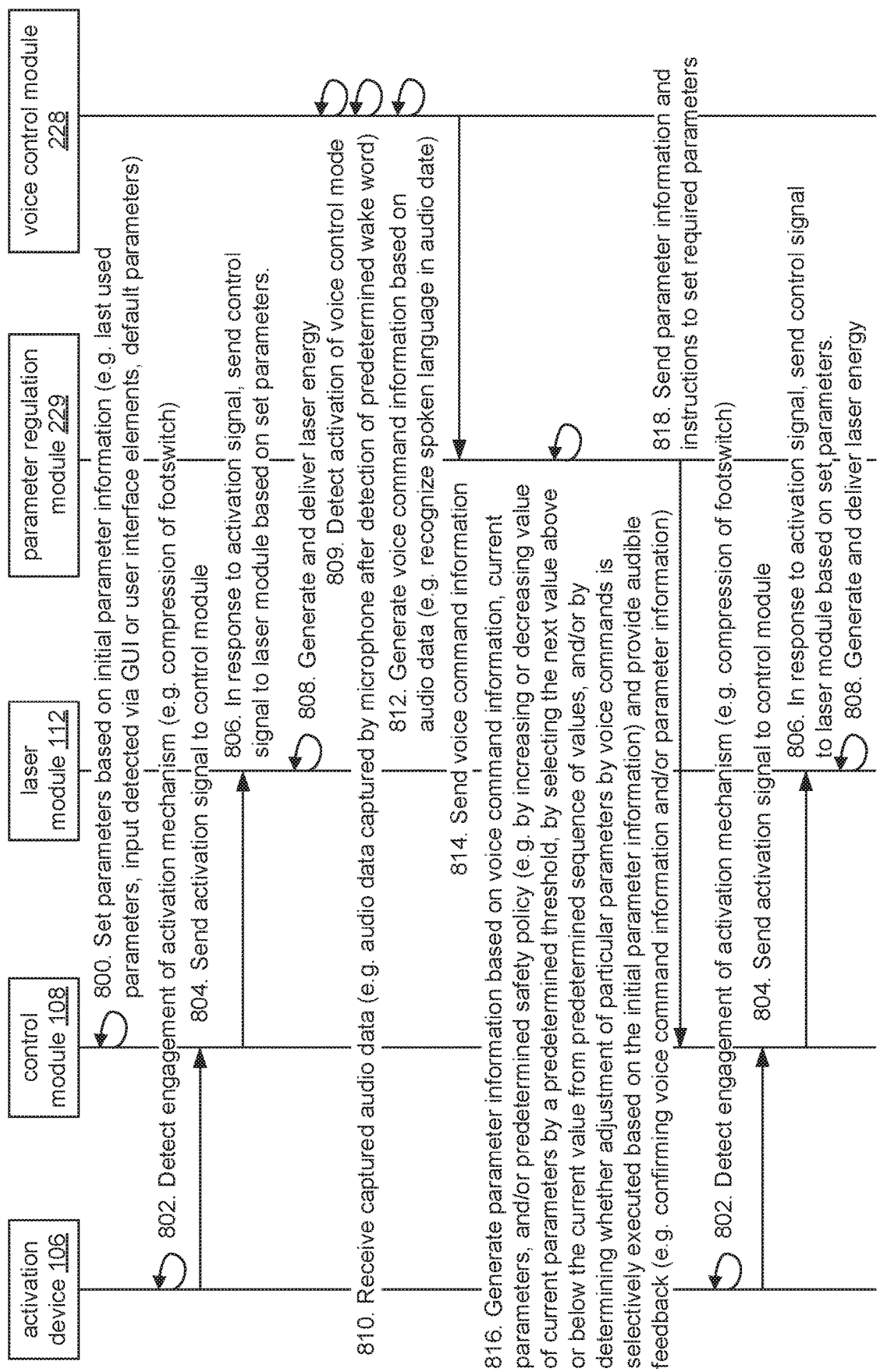
FIG. 7 is a sequence diagram illustrating the process by which parameters for delivered laser energy are set based on captured audio data according to the present invention.

FIG. 7 is a sequence diagram illustrating the process by which the parameters for delivered laser energy are set based on the captured audio data.

First, in step 800, the control module 108 sets initial parameters for the laser energy delivered by the laser module 112 based on the last used parameters, input detected via the GUI 232 or user interface 237, or predetermined default parameters.

In step 802, the activation device 106 detects engagement of the activation mechanism. In one example, the user's foot compresses a footswitch. In response, in step 804, the activation device 106 sends an activation signal to the control module 108.

In response to receiving the activation signal, the control module 108 in step 806 sends a control signal to the laser module 112.

In step 808, in response to receiving the control signal, the laser module 112 generates and emits the laser energy according to the parameters set by the control module 108.

In step 809, the voice control module 228 detects activation of a voice control mode based on configuration information and/or the predetermined safety policy which might specify situations in which voice control should be selectively executed.

In step 810, the voice control module 228 receives captured audio data. In one example, the mobile computing device 104, the laser console 103 or the user terminal 951, which continuously and in real time monitors audio data captured via the microphone 234 for a predetermined wake word programmed, detects the wake word and, in response, plays a tone through the speakers 236 prompting the user to say the voice command. The voice control module 228 then generates audio data based on sound that was captured after the wake word was detected and tone was played and sends the audio data to the voice control module 228.

In step 812, the voice control module 228 generates voice command information based on the captured audio data. In one example, the audio data includes spoken language such as the phrase "power up". The voice control module 228, for example via speech recognition processes, recognizes the phrase "power up" and translates the phrase into parameter information indicating that the power parameter should be incremented. The voice control module 228 sends the voice command information to the parameter regulation module 229 in step 812.

In step 229, the parameter regulation module 229 generates parameter information based on the voice command information, the current parameters, and/or the predetermined safety policy. In one example, the parameter regulation module 229 increases or decreases the current parameter value by a predetermined threshold and generates parameter information reflecting the higher or lower value. In another example, the parameter regulation module 229 selects the next highest or lowest value with respect to the current value from a predetermined sequence of possible parameter values. In another example, the parameter regulation module 229 determines whether setting of the particular parameters indicated in the voice command information should be allowed based on, for example, whether voice control of particular parameters is selectively executed.

In step 818, the parameter regulation module 229 sends the parameter information and instructions to set the required parameters to the control module 108.

Steps 802 through 808 then repeat as previously described, with the laser module 112 delivering laser energy based on the parameters.

Figure 8:
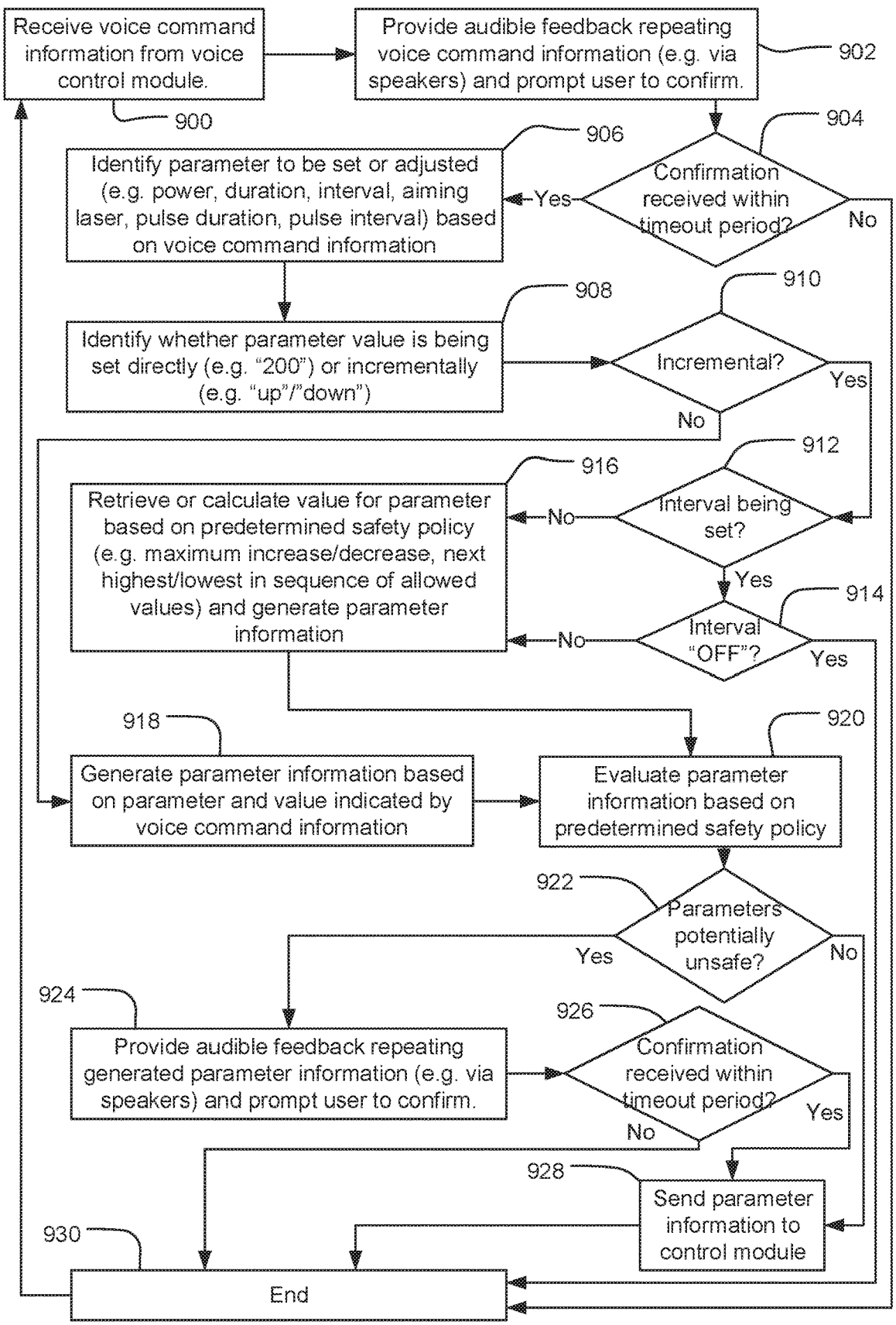
FIG. 8 is a flow diagram illustrating the process by which the parameter regulation module generates parameter information based on voice command information and a predetermined safety policy.

FIG. 8 is a flow diagram illustrating the process by which the parameter regulation module 229 generates parameter information based on the voice command information and the predetermined safety policy, which corresponds to the previously described step 816, for example.

In step 900, the parameter regulation module 229 receives the voice command information from the voice control module 228.

In step 902, the parameter regulation module 229 provides audible feedback repeating the voice command information (e.g. via the speakers 236) and prompts the user to confirm that the voice command information generated by the voice control module 228 and received from the parameter regulation module 229 accurately reflects the voice commands spoken by the user.

In step 904, it is determined whether a positive confirmation was received from the user (e.g. based on the voice control module 228 detecting a predetermined confirmation word via the microphone 234). If confirmation was not received after a predetermined time period, the process ends in step 930, and the parameter regulation module 229 does not proceed to change the parameters. In an alternative embodiment, the parameter regulation module 229 does not perform the confirmation of step 904 and simply proceeds after providing the audible feedback.

On the other hand, if confirmation was received within the predetermined time period, in step 906, the parameter regulation module 229 identifies the particular parameter (e.g. power, duration, interval, aiming beam, pulse duration, pulse interval) to be set or adjusted based on the voice command information. The parameter to be set/adjusted is based on, for example, which of a predetermined set of words associated with the parameters was detected and recognized by the voice control module 228.

Similarly, in step 908, the parameter regulation module 229 then identifies whether the parameter value is being set directly (e.g. based on recognized phrases corresponding to numerical values such as "200") or incrementally (e.g. based on recognized phrases corresponding to whether the value should be increased or decreased such as "up" or "down").

In step 910, it is determined whether the parameter is being set incrementally. If not, in step 918, the parameter regulation module 229 generates the parameter information based on the parameter being set and the value indicated by the voice command information.

On the other hand, if the parameter is being set incrementally, conditions such as the currently set parameters are evaluated to determine whether voice control should be selectively executed or whether the voice command should be ignored. For example, in step 912, it is determined whether the interval is the parameter being set, and if so, in step 914, it is determined whether the current setting for the interval parameter is "OFF" (or some other indication that an initial value for the interval has not been provided). If the interval parameter is set to "OFF", no change is made, the voice command is ignored, and the process ends in step 930.

On the other hand, if the interval is "ON" and is being adjusted, or if some other parameter value is being set or adjusted incrementally, in step 916, the parameter regulation module 229 retrieves or calculates a value for the parameter based on the predetermined safety policy. In one example, the policy sets a maximum increase or decrease value or percentage by which the current value is adjusted to calculate the new value. In another example, the policy provides a predetermined sequence of allowed values according to which the current value is incremented or decremented to the next value in the sequence. The parameter regulation module 229 then generates the parameter information.

Whether the parameter was set directly or incrementally, in step 920, the parameter regulation module 229 evaluates the parameter information based on the predetermined safety policy (for example, based on predetermined criteria in the safety policy for determining when parameters are potentially unsafe). This might include confirming that a parameter value set directly is within a certain difference threshold of the current value or that the value is within a predetermined range, among other examples.

In step 922 it is determined whether the parameters, including the parameter currently being set combined with the other parameters, create a potentially unsafe situation for the patient. If so, in step 924, the parameter regulation module 229 provides audible feedback repeating the generated parameter information (e.g. via the speakers 236) and prompts the user to confirm the parameter being set, possibly with a message informing the user that the parameters are potentially unsafe. In step 926, if no confirmation is received within a predetermined time period, no parameter changes are made, and the process ends in step 930.

On the other hand, if the parameters are not determined to be potentially unsafe, or if the user confirms the potentially unsafe parameters within the predetermined time period, in step 928, the parameter regulation module 229 sends the parameter information to the control module 108, which corresponds to previously described step 818.

Finally, the process ends in step 930. However, the process repeats continually, as the voice control module 228 continually generates voice command information based on audio data from the microphone 229 and sends the voice control information to the parameter regulation module 229.

Voice Command Examples

In general, the following table includes a set of exemplary voice commands interpreted by the voice command module 228, along with the appropriate action taken in response to the voice commands by the parameter regulation module 229. For these examples, the value N represents the current parameters, "N+1" and "N−1" are understood to denote the value N incremented or decremented, respectively, according to the safety policy. Similarly, the word "[TONE]" in the "Full Command Set" column indicates where in the sequence of spoken voice commands an audible tone would be played through the speakers 236 (e.g. a sound resembling a beep, chime) to prompt the user to proceed to say the rest of the voice command. The word "[MODE]" in the Audible Response column indicates where in the phrase a word corresponding to the current mode of the laser treatment system 100, such as "Treat" mode or "Standby" mode, among other examples.

More specifically, the Command column includes different voice commands (e.g. phrases spoken by the user) which are recognized by the voice control module 228. The Full Command Set column includes full sequences of wake words, audible tone prompts, and voice commands. The Audible Response column includes audible feedback (e.g. phrases) played through the speakers 236 in response to the voice control module 228 recognizing and interpreting the voice commands. Finally, the System Action column includes actions performed, for example, by the parameter regulation module 229 in response to the voice control module 228 recognizing the voice commands in the Commands column.

| Command | Full Command Set | Audible Response | System Action |
| --- | --- | --- | --- |
| "Enter Treat" | "OK Norlase" [TONE] "Enter Treat" | "Treat Mode Selected" | Places the system into a "Treat" Mode |
| "Enter Standby" | "OK Norlase" [TONE] "Enter Standby" | "Standby Mode Selected" | Places the system into the "Standby" Mode |
| "Power Up" | "OK Norlase" [TONE] "Power Up" | "Power at [N + 1]" | Increases power one increment from current setting |
| "Power Down" | "OK Norlase" [TONE] "Power Down" | "Power at [N − 1]" | Decreases power one increment from current setting |
| "Duration Up" | "OK Norlase" [TONE] "Duration Up" | "Duration at [N + 1]" | Increases Duration one increment from current setting |
| "Duration Down" | "OK Norlase" [TONE] "Duration Down" | "Duration at [N − 1]" | Decreases Duration one increment from current setting |
| "Interval Up" | "OK Norlase" [TONE] "Interval Up" | "Interval at [N + 1]" | Increases Interval one increment from current setting |
| "Interval Down" | "OK Norlase" [TONE] "Interval Down" | "Interval at [N − 1]" | Decreases Interval one increment from current setting |
| "Aiming Beam Up" | "OK Norlase" [TONE] "Aiming Beam Up" | "Aiming Beam at [N + 1]%" | Increases aiming beam 10% |
| "Aiming Beam Down" | "OK Norlase" [TONE] "Aiming Beam Down" | "Aiming Beam at [N − 1]%" | Decreases aiming beam 10% |
| "Pulse Count" | "OK Norlase" [TONE] "Pulse Count" | "Pulse Count at N" | Will call out the current number of laser pulses delivered |
| "System Status" | "OK Norlase" [TONE] "System Status" | "[Mode] Mode selected, Power at [N], Duration at [N], Interval at [N], Pulse Count at [N]" | Will call out the current settings for Laser Status, Power, Duration, Interval and Pulse Count. |

In one example, in order to execute the "Enter Treat" voice command, the user speaks the wake word "OK Norlase." An audible tone is then played through the speakers 236, after which the user speaks the voice command "Enter Treat." In response to the voice control module 228 recognizing and interpreting the voice command, the parameter regulation module 229 plays the audible feedback phrase "Treat Mode Selected" and then proceeds to place the system into the "Treat" mode, during which parameters can be adjusted and laser energy can be delivered.

In another example, in order to execute the "Power Up" voice command, the user speaks the wake word "OK Norlase." An audible tone is then played through the speakers 236, after which the user speaks the voice command "Power Up." In response to the voice control module 228 recognizing and interpreting the voice command, the parameter regulation module 229 plays the audible feedback phrase "Power at [N+1]", referring to the new value of the power parameter and increases the power one increment from the current setting, according to the safety policy and other processes described, for example, with respect to FIG. 8. For example, if the power is currently set at 120, the audible response would be "Power at 130" to indicate that the power parameter has been increased to 130.

Finally, in yet another example, in order to execute the "System Status" voice command, the user speaks the wake word "OK Norlase." An audible tone is then played through the speakers 236, after which the user speaks the voice command "System Status." In response to the voice control module 228 recognizing and interpreting the voice command, the parameter regulation module 229 plays the informational audible feedback phrase "[Mode] Mode selected, Power at [N], Duration at [N], Interval at [N], Pulse Count at [N]," referring respectively to the current mode setting and the current values of the power, duration, interval and pulse count.

While this invention has been particularly shown and described with references to preferred embodiments thereof, it will be understood by those skilled in the art that various changes in form and details may be made therein without departing from the scope of the invention encompassed by the appended claims.

What is claimed is:
1. A system for delivering laser energy to an eye of a patient, the system comprising:
   a microphone for capturing audio data;
   a voice control module for receiving the captured audio data and generating voice command information based on the captured audio data, wherein the voice control module generates the voice command information by recognizing spoken language indicating 1) whether a pulse duration should be incrementally increased or decreased; and 2) whether a power level should be incrementally increased or decreased;
   a parameter regulation module for generating parameter information based on the voice command information;
   a control module for receiving the parameter information and setting the parameters for the delivered laser energy based on the parameter information;

a speaker for providing audible feedback confirming the voice command information; and a footswitch activation device for activating the delivery of the laser energy.

2. The system as claimed in claim 1, wherein the voice control module generates the voice control information by recognizing spoken language indicating values for the parameters.

3. The system as claimed in claim 1, wherein the microphone captures the audio data in response to detecting a predetermined wake word.

4. The system as claimed in claim 1, wherein the voice control module executes on a mobile computing device of a body-mounted laser-indirect ophthalmoscope system, a laser console of a laser-indirect ophthalmoscope system, and/or a user terminal of an ophthalmic laser treatment system.

5. The system as claimed in claim 1, wherein the parameter regulation module executes on a mobile computing device of a body-mounted laser-indirect ophthalmoscope system, a laser console of a laser-indirect ophthalmoscope system, and/or a user terminal of an ophthalmic laser treatment system.

6. The system as claimed in claim 1, wherein the parameter regulation module generates the parameter information based on current values for the parameters to be set and/or a predetermined safety policy.

7. The system as claimed in claim 6, wherein the safety policy indicates maximum values and/or percentages by which the current values for the parameters can be increased and/or decreased to calculate new values for the parameters.

8. The system as claimed in claim 6, wherein safety policy indicates predetermined sequences of possible values for the parameters.

9. The system as claimed in claim 1, wherein the safety policy indicates whether particular parameters should be selectively executed based on current parameters.

10. The system as claimed in claim 1, wherein the voice control module generates the voice command information based on voice recognition processes executed locally and/or on a remote host system.

11. A method for delivering laser energy to an eye of a patient using an ophthalmic laser treatment system, the method comprising:

capturing audio data;

generating voice command information based on the captured audio data by recognizing spoken language indicating 1) whether a pulse duration should be incrementally increased or decreased; and 2) whether a power level should be incrementally increased or decreased;

generating parameter information based on the voice command information;

setting parameters for the delivered laser energy based on the parameter information;

providing audible feedback confirming the voice command information; and enabling activation of the delivery of the laser energy via a footswitch activation.

12. The method as claimed in claim 11, further comprising generating the voice command information by recognizing spoken language indicating values for the parameters.

13. The method as claimed in claim 11, further comprising capturing the audio data in response to detecting a predetermined wake word.

14. The method as claimed in claim 11, wherein the ophthalmic laser treatment system is a body-mounted laser-indirect ophthalmoscope system, a laser console of a laser-indirect ophthalmoscope system, and/or a user terminal of an ophthalmic laser treatment system.

15. The method as claimed in claim 11, further comprising generating the parameter information based on current values for the parameters to be set and/or a predetermined safety policy.

16. The method as claimed in claim 15, wherein the safety policy indicates maximum values and/or percentages by which the current values for the parameters can be increased and/or decreased to calculate new values for the parameters.

17. The method as claimed in claim 15, wherein the safety policy indicates predetermined sequences of possible values for the parameters.

18. The method as claimed in claim 15, wherein the safety policy indicates whether particular parameters should be selectively executed based on current parameters.

19. The system as claimed in claim 1, wherein the voice control module generates the voice command information by recognizing spoken language indicating whether the system should be placed in a standby mode or placed in a treat mode.

20. The system as claimed in claim 1, wherein the voice control module generates the voice command information by recognizing spoken language indicating whether increasing or decreasing an aiming beam.

21. The system as claimed in claim 1, wherein the voice control module generates the voice command information by recognizing spoken language indicating a number of pulses to be delivered.

22. The system as claimed in claim 1, wherein the audible feedback includes repeating back the voice command information.

23. The system of claim 1, wherein valid voice commands for pulse duration and power level parameters are limited to whether to adjust the parameters up or down.

24. The system of claim 7, wherein the safety policy sets a predetermined maximum percentage for increasing or decreasing the current values, and the parameter regulation module only increases the pulse duration and the power level by the predetermined maximum percentage based on the voice command information.

25. The system of claim 23, wherein the predetermined maximum percentage is 20%.

26. The system of claim 1, wherein the parameter regulation module evaluates safety of the generated parameter information based on predetermined safety criteria in the safety policy and provides audible feedback informing a user of potentially unsafe parameters.

27. The system of claim 26, wherein the audible feedback informing the user of potentially unsafe parameters includes a message informing the user that the parameters are potentially unsafe.

28. The system of claim 2, wherein the parameter regulation module evaluates the safety of parameter values that were set directly via the spoken language indicating the values for the parameters by confirming that the parameter values that were set directly are within a certain difference threshold of current parameter values and/or that the parameter values that were set directly are within a predetermined range.

29. The system of claim 1, wherein the parameter regulation module determines whether parameter values being set via the voice command information combined with other parameters create a potentially unsafe situation.

30. The system of claim 29, wherein the parameter regulation module prompts a user to confirm parameter changes indicated by the voice command information in response to determining that the parameter values being set via the voice command information combined with other parameters create a potentially unsafe situation, and the parameter regulation module makes no changes to current parameters in response to determining that positive confirmation was not received within a predetermined time period.

31. The system of claim 1, wherein the parameter regulation module prompts the user for extra confirmation of the voice command information in response to determining that parameters indicated by the voice command information are potentially unsafe according to the safety policy.

32. The system of claim 9, wherein the parameter regulation module generates the parameter information based on the safety policy indicating whether particular parameters should be selectively executed based on current parameters by, upon determining that the voice command information indicates an adjustment to an interval parameter, ignoring the voice command information in response to determining that an initial value for the interval parameter was not previously provided for a current treatment session.

33. The system of claim 8, wherein the parameter regulation module generates the parameter information based on the safety policy by incrementing or decrementing the current values for the parameters to the next values in the predetermined sequences of possible values indicated by the safety policy.

34. A system for delivering laser energy to an eye of a patient, the system comprising:
   a microphone for capturing audio data;
   a voice control module for receiving the captured audio data and generating voice command information based on the captured audio data, wherein the voice control module generates the voice command information by recognizing spoken language indicating 1) whether a pulse duration should be incrementally increased or decreased; and 2) whether a power level should be incrementally increased or decreased;
   a parameter regulation module for generating parameter information, based on the voice command information, current values for the parameters to be set, and a predetermined safety policy, by iterating through sequences of predetermined values indicated by the safety policy for particular parameters and selecting the next higher or lower values in the predetermined sequences with respect to the current values, or by calculating adjusted values for the parameters by increasing or decreasing the current values for the parameters by predetermined maximum values and/or percentages indicated by the safety policy for the parameters;
   a control module for receiving the parameter information and setting the parameters for the delivered laser energy based on the parameter information; and
   a footswitch activation device for activating the delivery of the laser energy based on the parameters set by the control module.

* * * * *